United States Patent
Connesson et al.

(10) Patent No.: US 10,508,979 B2
(45) Date of Patent: Dec. 17, 2019

(54) PURE BENDING MECHANICAL TEST DEVICE AND METHOD FOR IMPLEMENTING SAME

(71) Applicant: Universite Grenoble Alpes, Saint Martin d'Heres (FR)

(72) Inventors: Nathanael Connesson, Grenoble (FR); Yohan Payan, Allevard (FR); Gabriel Antehrieu, Grenoble (FR); Denis Favier, La Tronche (FR)

(73) Assignee: UNIVERSITE GRENOBLE ALPES, Saint-Martin-d'Heres (FR)

(*) Notice: Subject to any disclaimer, the term of this patent is extended or adjusted under 35 U.S.C. 154(b) by 263 days.

(21) Appl. No.: 15/322,591

(22) PCT Filed: Jul. 3, 2015

(86) PCT No.: PCT/EP2015/065250
§ 371 (c)(1),
(2) Date: Dec. 28, 2016

(87) PCT Pub. No.: WO2016/001426
PCT Pub. Date: Jan. 7, 2016

(65) Prior Publication Data
US 2018/0202909 A1    Jul. 19, 2018

(30) Foreign Application Priority Data
Jul. 4, 2014 (FR) .................................. 14 56479

(51) Int. Cl.
*G01N 3/20* (2006.01)
(52) U.S. Cl.
CPC ....... *G01N 3/20* (2013.01); *G01N 2203/0023* (2013.01); *G01N 2203/0067* (2013.01);
(Continued)

(58) Field of Classification Search
CPC .. G01N 3/20; G01N 3/34; G01N 3/32; G01N 2203/0023; G01N 2203/0073;
(Continued)

(56) References Cited

U.S. PATENT DOCUMENTS

| | | | | | |
|---|---|---|---|---|---|
| 1,443,877 | A | * | 1/1923 | Guelbaum | ............... G01N 3/20 73/789 |
| 2,170,640 | A | * | 8/1939 | Kenyon | ................... G01N 3/32 73/810 |

(Continued)

FOREIGN PATENT DOCUMENTS

| | | | |
|---|---|---|---|
| FR | 2843633 A1 | 2/2004 | |
| GB | 409805 A * | 5/1934 | ............... G01N 3/32 |

(Continued)

OTHER PUBLICATIONS

Hoefnagels, J.P.M. et al. "A miniaturized contactless pure-bending device for in-situ SEM failure analysis" In: Experimental and Applied Mechanics, vol. 6, 2011, pp. 587-596.

(Continued)

*Primary Examiner* — Nathaniel J Kolb
(74) *Attorney, Agent, or Firm* — Pearne & Gordon LLP

(57) ABSTRACT

A device for performing a mechanical four-point bending test on a test piece and to a method for using one such device. The device comprises: a) structure for holding a first end of the test piece (27; 127; 28; 128) and structure for holding a second end of the test piece (30, 31); b) traction wire (25) and converting structure (16, 116) for converting a translational movement of said traction means into a rotational movement; c) conversion structure (26; 27; 126; 127) for converting said rotational movement into bending deformation of the test piece. Said conversion structure comprises at least one first Cardan joint (26; 126), connected to the structure for holding the first end of the test piece.

20 Claims, 6 Drawing Sheets

(52) U.S. Cl.
CPC ............... *G01N 2203/0206* (2013.01); *G01N 2203/028* (2013.01); *G01N 2203/0282* (2013.01); *G01N 2203/0435* (2013.01)

(58) Field of Classification Search
CPC ... G01N 2203/0037; G01N 2203/0005; G01N 2203/0007
USPC .................................................. 73/865.9, 866
See application file for complete search history.

(56) References Cited

U.S. PATENT DOCUMENTS

| | | | | |
|---|---|---|---|---|
| 5,022,273 A | * | 6/1991 | Evans | ............... G01N 3/20 73/849 |
| 5,231,882 A | * | 8/1993 | Bertele | ............... G01N 3/32 73/852 |
| 2005/0109074 A1 | * | 5/2005 | Olsen | ............... B21D 7/12 72/295 |
| 2013/0327152 A1 | * | 12/2013 | Chen | ............... G01N 3/08 73/818 |

FOREIGN PATENT DOCUMENTS

| | | |
|---|---|---|
| GB | 409805 A | 5/1934 |
| RU | 2160892 C2 * | 12/2000 |

OTHER PUBLICATIONS

Bechle, Nathan J. et al. "Localization in NiTi tubes under bending" In: International Journal of Solids and Structures, 2014, 967-980.
International Search Report for PCT/EP2015/065250 dated Sep. 25, 2015.
FR 1456479 Search Report dated Feb. 24, 2015.

* cited by examiner

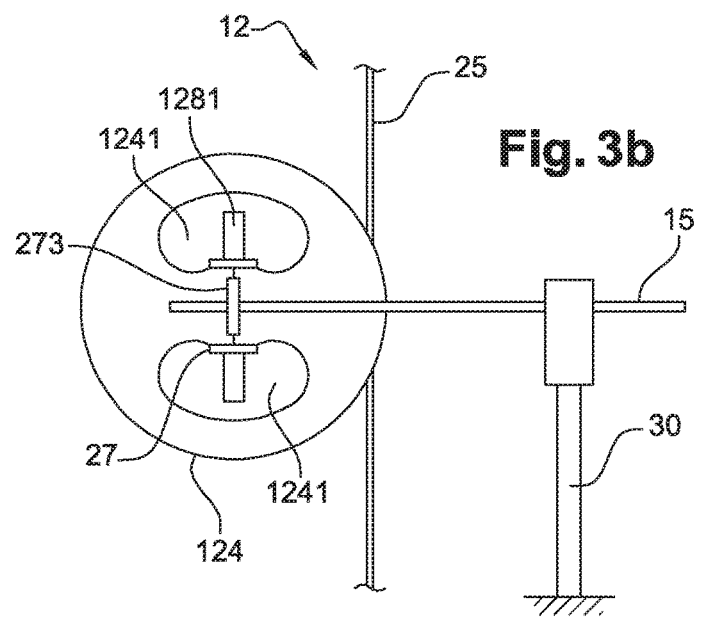
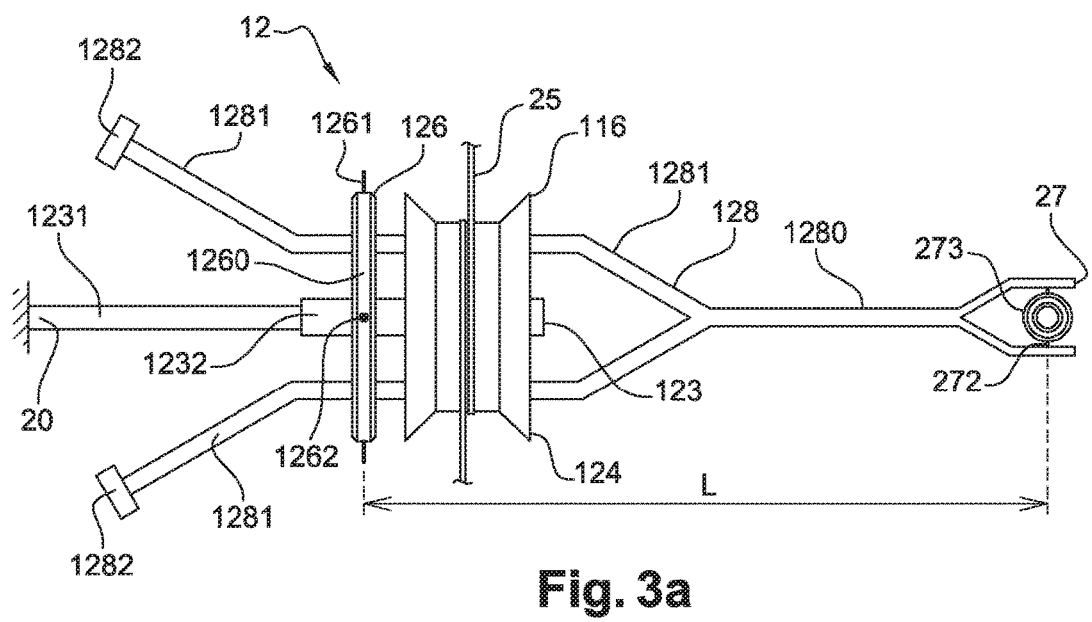

PURE BENDING MECHANICAL TEST DEVICE AND METHOD FOR IMPLEMENTING SAME

TECHNICAL FIELD

The invention relates to a pure bending, also called circular bending, mechanical test device and a test method implementing such a device.

The term pure bending is a recognised term in materials science and pure bending tests are widely used in experimental mechanics. The theory describing them is theoretically well established. These tests are the subject of numerous analytical and numerical studies. Pure bending tests induce a strain gradient in the thickness of the loaded test pieces (ranging from traction to local compression) while the bending moment applied is homogeneous along the test piece.

In practice, during the bending test on a test piece, the test piece is subjected to parasitic shear and torsion stresses. It is nevertheless possible to speak of 'pure bending' when the moments induced by these parasitic stresses are made negligible compared with the bending moment to which the test piece is subjected.

State of the Prior Art

In order to be able to compare experimental data with theoretical/digital results, properly managing the load to which the sample is subjected is vital. For this reason, particular care must be taken during experiments in order to ensure that the whole of the area of interest of the sample is properly loaded in pure bending during tests. In fact, if parasitic stresses are induced by the device (torsion, shearing stresses), the bending moment will not be homogeneous all along the useful zone of the test piece. Lack of knowledge of the exact local load to which the sample is subjected makes the results non-exploitable. In practice, it is very difficult to load perfectly a test piece in pure bending. Numerous precautions have to be taken. It will be considered herein that the test piece is loaded in pure bending when parasitic stresses are negligible and do not impede exploitation of the experimental results.

Various pure bending devices have been described in the scientific literature and in patents.

In certain "four-point" bending devices of the prior art, a test piece (also called sample) is arranged in suspension between two points of a fixed support. Two point-supports of a moveable part are placed in contact with the test piece between the two points of the fixed support and stresses are applied on the test piece. The test piece is then deformed in pure bending between the two point-supports. However, in these devices, the maximum movement threshold in pure bending of the centre of the sample is less than its thickness or the order of magnitude thereof. Bending causing movement of the centre of the sample greater than this threshold would bring about sliding of the sample at the level of the support and would falsify measurements of the moment. During the study of the mechanical properties of slender samples, movement of the centre of the sample of this order of magnitude does not make it possible to load the samples in a sufficient deformation domain: a system enabling large movements is necessary to attain high deformations. These measurements are of vital interest for slender samples or samples manufactured from super-elastic materials, or when the manufacturing method thereof does not make it possible to obtain other geometries. In the context of the present application, a slender sample (also called slender test piece) must be understood as being a sample of which the length/diameter ratio is greater than or equal to 5, preferentially but not in a limiting manner between 5 and 20, for example 8, 10 or 12.

Certain other bending devices, for example those described hereafter, implementing a "four-point" bending method in which a test piece to test is maintained between two rotationally controlled supports. However, said devices only make it possible to load part of the sample in pure bending for small movements and none seems able to attain low radiuses of curvature. Typically, these devices make it possible to attain radiuses of curvatures of the order of 10 cm.

Pure bending characterisation of slender samples requires the capacity of attaining small radiuses of curvature. Such an aptitude is not required for squat test pieces, that is to say for example of length/diameter ratio less than 5, or when the test does not require large deformations to be attained: during a bending test, for a fixed radius of curvature, the larger the characteristic diameter of the sample, the greater the maximum deformation undergone by the material, typically on the exterior surface. Thus, to reach the same state of deformation on a small sample, the radius of curvature required is much less.

Several publications or patented devices enable samples of reduced size to be studied.

In the scientific literature, the document Kyriakides et al. (Localization in NiTi tubes under pure bending, N. Bechle, J. S. Kyriakides, International Journal of Solids and Structures, 2014, Vol. 51, pp 967-980) describes results on tubes of 3 mm diameter. This bending device comprises however several limitations. The rotational actuators are fixed: the length of loaded material increases during a bending test. The sample slides in the ball sleeves, which induces friction stresses in the axis of the sleeves. This kinematic, associated with resistances to movement, makes the bending moment vary along the test piece. This variation in the moment along the test piece changes during the test: friction has little impact for a slightly deformed test piece, that is to say practically rectilinear, but can induce larges variations in the bending moment along the test piece when the shape of the deformed test piece approaches a half circle. This device thus does not make it possible to obtain a pure bending moment. This phenomenon particularly impacts measurements for small radiuses of curvature. In addition, the radiuses of curvature that can be attained are too important for samples of diameter of the order of 1 mm or less.

The device described in the document of Hoefnagels et al. (A miniaturized contactless pure-bending device for in-situ SEM failure analysis, J. P. M Hoefnagels, C. A. Buizer, M. G. D Geers, Experimental and Applied Mechanics, 2011, Vol. 6, pp 587-596) makes it possible in theory to load the sample in pure bending: the device imposes on the sample a kinematic of its ends corresponding to that of pure bending under the hypothesis of homogenous mechanical behaviour all along the test piece. The major limit of this device resides in the hypotheses required for the definition of the kinematic of the system. In fact, if the mechanical properties of the sample are heterogeneous, the case frequently encountered experimentally, the kinematic imposed by the mechanism will not induce pure bending along the length of the sample. The stresses, the state of deformation and the state of local strain in the material will then be unknown and the experimental results could not be analysed correctly.

The device described in the document FR2843633 meets the conditions making it possible to load two test pieces in pure bending. The motors that load the two test pieces are supported by various means, such that they can move freely in space. This freedom of movement enables them to avoid the appearance of parasitic stresses, which ensures a homogeneous state of strain in the loaded samples. However, several limitations are imposed by this system. Firstly, in the configuration where the motors are suspended by cables so that stresses due to the movements of the motors are zero, the length of the cables must be theoretically infinite and the cables have to be insensitive to movements of the ambient air. This thus makes the device relatively bulky, not very transportable, and not very suited to a low ceiling room. Generally speaking, this device is difficult to adapt on a conventional test machine. In addition, it is above all intended for samples of flat geometry such as plates and requires simultaneously loading two rigorously identical samples (geometry, homogeneity of material between the two samples, etc.). These constraints are awkward to obtain experimentally.

The document US 2013/0327152 A1 describes a buckling device in which a test piece is subjected to compression forces. The moments to which the test piece are subjected are different along the test piece because the moment results from the multiplication of stress by distance.

The invention thus aims to propose an improved mechanical device making it possible to load a sample, preferably slender, or a test piece, preferably slender, in bending.

Advantageously, such a device is simple and inexpensive.

DESCRIPTION OF THE INVENTION

Thus, the invention relates to a device for performing a four-point mechanical bending test on a test piece, said device comprising:

a) means for holding a first end of a test piece and means for holding a second end of the test piece;

b) traction means and converting means for converting a translational movement of said traction means into a rotational movement;

c) conversion means for converting said rotational movement into bending deformation of the test piece, said conversion means comprising at least one first Cardan joint, connected to the means for holding the first end of the test piece.

Cardan joint is for example taken to mean an example of embodiment of a finger joint.

Preferably, a shaft connects the first Cardan joint to the means for holding the first end of the test piece.

During bending deformation of a test piece, the use of a Cardan joint combined with the conversion means makes it possible to compensate parasitic shearing stresses appearing in the test piece by a free movement and of large amplitude of the end of a test piece. This movement operates up to the disappearance of the stress giving rise thereto. When mechanical balancing is attained, parasitic torsion and shear stresses in the test piece are negligible. It is thus possible to test in pure bending test pieces over a particularly important range of radiuses of curvature, from linear geometry up to very small radiuses of curvature, less than 1 cm, without the deformation of the test piece being hindered by the components of the device.

The invention may in addition be used on filiform samples of diameter equal to or less than 1 mm, for example comprised between 0.1 mm and 1 mm.

During a bending test using the device according to the invention, the tested length of a test piece is constant and is subjected to a pure (homogeneous) bending moment over its whole length. The bending moment is constant at all points of the test piece. The term pure bending is used if the parasitic shearing and torsion stresses to which the test piece is subjected induce moments and gradients of moments negligible for the measurements (and thus that the moment is homogeneous over the whole length of the test piece). This enables uniform deformation of the test piece, that is to say in an arc of circle in the elastic domain of the material of the test piece if the material is homogeneous. It is possible notably to qualify the deformation as uniform if the following hypotheses are met: pure and homogeneous moment, constant section, homogeneous material.

Whatever the behaviour of the test piece and its heterogeneity of materials, the margin for error is particularly small in the measurement of the bending moment that is applied to it, of the order of $10^{-4}$ N·m for a device implemented by the applicant.

The use of a Cardan joint further makes it possible to obtain a particularly simple, inexpensive structure having a reduced number of components compared to that which exists.

Moreover, this structure has the advantage of being useable with a conventional traction machine.

Advantageously, the conversion means comprise a second Cardan joint.

Said second Cardan joint may itself comprise a bearing, for example a ball bearing.

Said bearing may be common to the means for holding a first end of a test piece and to the conversion means.

Alternatively or cumulatively, the second Cardan joint may comprise other organs forming a low friction pivot link and which are common to the means for holding a first end of the test piece and to the conversion means, such as metal tip on sapphire links, or instead needle links pivot-mounted in respective drillings.

The second Cardan joint forms a low friction articulation and makes it possible to minimise further the impact of parasitic stresses.

Alternatively, the first Cardan joint is connected to the means for holding a first end of the test piece, the means for holding a first end of the test piece comprising at least one organ provided with a drilling intended to receive one end of a test piece. The organ concerned is located behind the first Cardan joint in the kinematic chain connecting the actuating wire to the test piece, starting from the actuating wire. It is for example an arm fixed onto an arch of the first Cardan joint.

This structure is particularly advantageous in terms of costs. The link clearances between the test piece and the circumference of the drilling advantageously replace the second Cardan joint. Friction between the test piece and the circumference of the drilling is entirely negligible for the measurement of the bending moment.

The converting means may comprise a wheel, the first Cardan joint connecting the wheel and the means for holding a first end of the test piece.

In a particular example of embodiment, the first Cardan joint is connected to at least one structure, comprising for example an arm, which traverses the converting means. This structure may further comprise balancing means so that the weight of the device does not weigh down the loaded sample, for example bear a balancing mass. This structure may further comprise two branches arranged in a fork shape, the converting means comprising a wheel, the wheel being provided with two through openings, each branch traversing respectively one of the two openings and being able to be connected to the first Cardan joint.

The above device may further comprise measuring means for measuring stress exerted on the traction means or measuring means for measuring torsion stress on a downstream organ to which the first Cardan joint is connected.

The invention also relates to a mechanical bending test system, comprising a traction machine and a mechanical bending test device as described above, the traction machine comprising a traction mechanism connected to the traction means of the test device, the mechanism being configured to apply a traction force on these traction means.

The invention also relates to a method for performing a mechanical bending test on a test piece using a mechanical test device as described above, comprising the steps of:

placing a first end of the test piece in the means for holding a first end of a test piece, and a second end of the test piece in the means for holding a second end of the test piece;

applying a tension on the traction means;

determining the bending moment by measuring means to measure stress exerted on the traction means or by measuring means for measuring torsion stress on a downstream organ to which the first Cardan joint is connected.

Advantageously, the placing of the test piece comprises the following steps:

tightening a first ring onto a first end of the test piece, against the means for holding the first end of a test piece;

tightening a second ring onto a second end of the test piece, against the means for holding the second end of the test piece;

the first and second rings being tightened onto the respective ends of the test piece outside of the zone comprised between the means for holding the first and the second ends of the test piece.

A device or a method according to the invention advantageously applies to a slender sample, the length/diameter ratio of which is greater than or equal to 5, for example comprised between 5 and 20.

A device or a method according to the invention makes it possible to obtain a large deformation, of the test piece, of at least several %, for example at least 3% or at least 5%, this being a function of the nature of the material. For example, a deformation of 5% on a test piece made of steel is large, a deformation comprised between 10% and 15% for NiTi is also large.

BRIEF DESCRIPTION OF THE DRAWINGS

The invention will be better understood on reading the detailed description that follows of examples of the non-limiting implementation thereof, and by examining the appended partial and schematic figures, in which:

FIG. 2a is a side view of a variant of the device of FIG. 1a;

FIGS. 3a and 3b are side and front views of another variant of the device of FIG. 1, FIG. 3b showing a test piece at rest, here rectilinear, housed in the device;

FIG. 7 is a side view of another variant of the device of FIG. 1a;

DETAILED DESCRIPTION OF PARTICULAR EMBODIMENTS

Figure 1A:
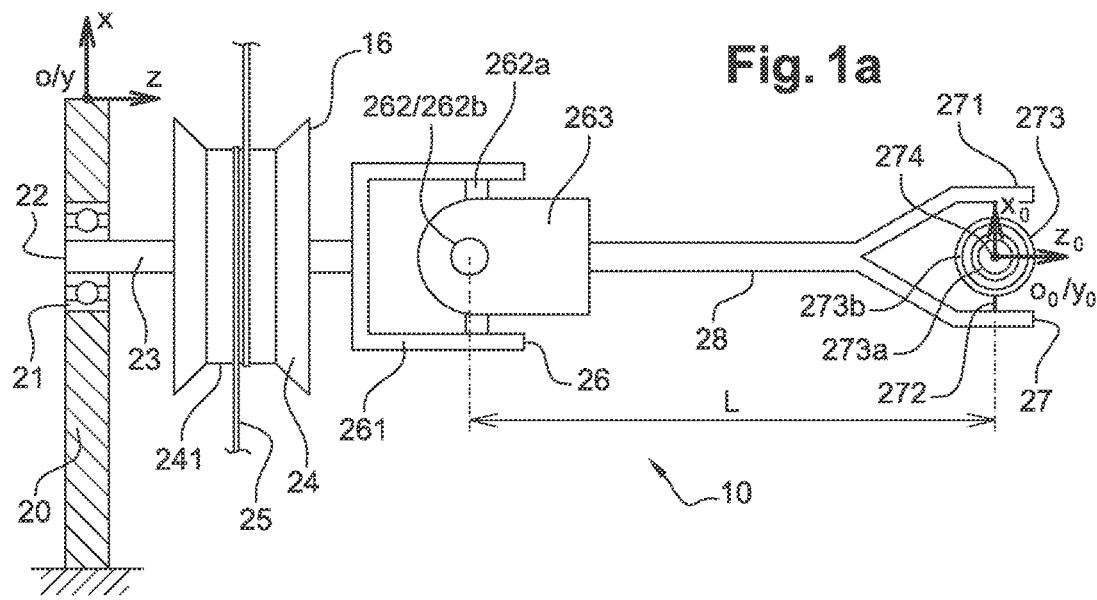
FIG. 1a is a side view of a part of a test device according to the invention.
Figure 1B:
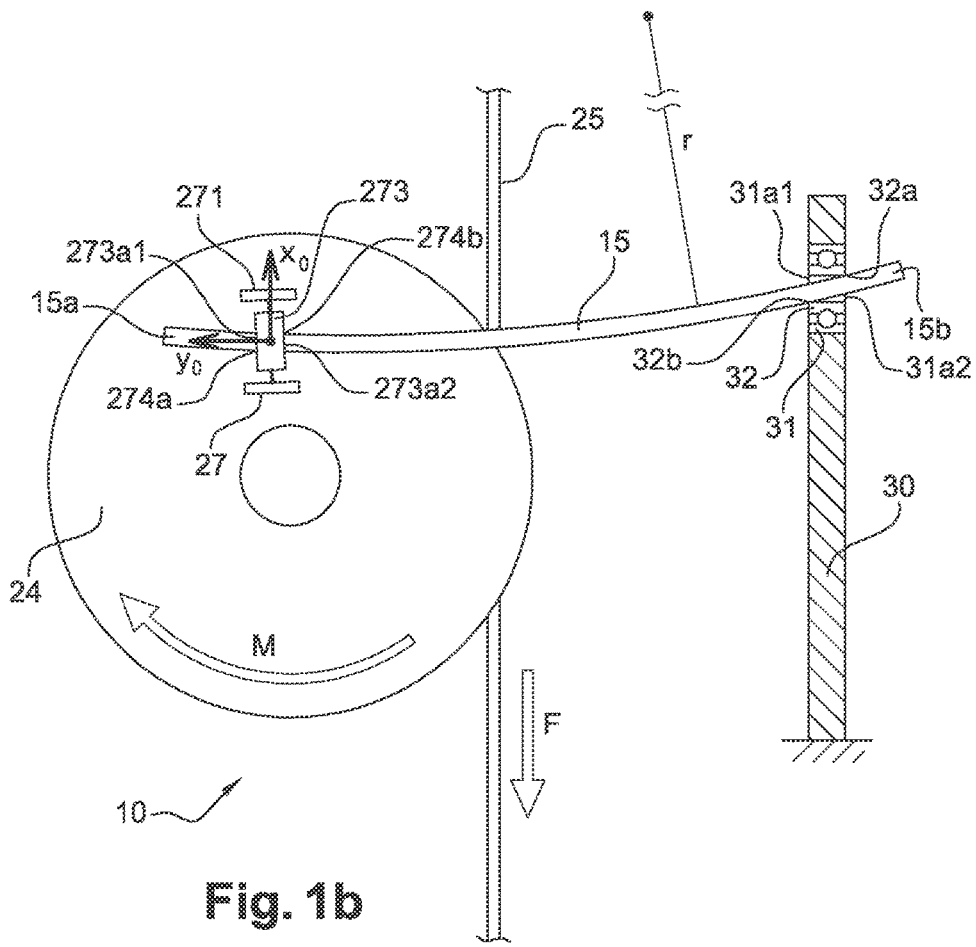
FIG. 1b is a front view of the device of FIG. 1a showing a test piece in a particular bent state, during a test.

A four-point bending test device 10 is illustrated in FIGS. 1a and 1b.

The device 10 here comprises a stand 20, a pulley 16 or pulley system, an actuating wire 25, two Cardan joints 26 and 27, a shaft 28 (or arm) which here connects the two Cardan joints 26 and 27, and a support 30 (FIG. 1b).

A test piece 15, also called sample, the bending properties of which are to measure, is also illustrated at rest in FIG. 3b or in bending in FIG. 1b. The test piece 15 may be for example a wire or a tube, the diameter of which is less than 1 mm, for example metal but not exclusively. The test piece 15 may be a slender test piece, the length/diameter ratio of which is, for example, greater than or equal to 5, preferentially but not in a limiting manner comprised between 5 and 20, for example equal to, or of the order of, 8, or 10 or 12.

As will be seen later with reference to FIG. 1b, when the test piece 15 is in bending, the test piece 15 is in four-point contact with the device 10, namely the points 32a, 32b, 274a and 274b in the embodiment represented in FIG. 1b.

The stand 20 comprises a bearing 21, here a ball bearing, delimiting an orifice 22. Similarly, the support 30 comprises a bearing 31, here a ball bearing, delimiting an orifice 32. The stand 20 and the support 30 may be either directly integral with each other, that is to say manufactured from a same block, or fixed to each other, or instead both fixed to a fixed stand of an external test machine such as a traction machine. The stand 20 and the support 30 serve for example as fixed reference points during the bending tests.

The pulley 16 here comprises a shaft 23 (or arm) and a wheel 24. The wheel 24 is fixed onto the shaft 23 and is rotationally integral therewith.

The actuating wire 25 is wound on a central groove 241 which the wheel 24 comprises. The central groove 241 preferentially has a flat bottom so that the actuating wire does not undergo sliding in the groove 241, so that the wire does not overlap on itself, and so that the distance between the centre of rotation of the pulley and the wire remains constant whatever the angular position. A sliding or an overlapping of the wire on itself, like contact of the actuating wire with itself, would risk causing friction and measurement errors. The term actuating wire may strictly speaking designate a wire or a cable in the case of a device of greater size. The shaft 23 is housed in the orifice 22 and fixed onto the internal track of the bearing 21. The shaft 23 and the wheel 24 are thus rotationally moveable with respect to the stand 20.

The actuating wire 25 is for example fixed by a first end to a traction mechanism of an external traction machine, not illustrated. This wire 25 is used for converting a translational movement, here provided by the traction machine, into a rotational movement of the wheel 24 and of the shaft 23.

The other end of the actuating wire 25 may for example be left free, or instead fixed to a moveable part serving for the translation of the wire 25 of the traction mechanism.

A first three-dimensional Oxyz reference system is defined fixed with respect to the stand 20 (FIG. 1a), the z axis coinciding with the longitudinal orientation of the shaft 23 and the x and y axes being transversal to each other and to the z axis.

A second three-dimensional $O_0x_0y_0z_0$ reference system is defined fixed with respect to the shaft 28 (FIG. 1a), the $z_0$ axis coinciding with the longitudinal orientation of the shaft 23 and the $x_0$ and $y_0$ axes being transversal to each other and to the $z_0$ axis.

The z axis also coincides with the $z_0$ axis of the arm 28 when this is in the position illustrated in FIG. 1a, whereas the x and y axes are parallel respectively to $x_0$ and $y_0$.

It should be understood that the orientation of the different components of the device 10 may vary during a bending test and no longer coincide with the axes of the Oxy reference system.

The first Cardan joint 26 is here of cross-piece type.

The joint 26 represented comprises two arches 261 and 263 (that is to say two U-shaped pieces) and a cross-piece 262. The cross-piece 262 comprises two branches 262a and 262b transversal to each other and joined in their middle. In the position of the shaft 28 illustrated in FIG. 1a, the branch 262a is oriented along the x axis and the branch 262b is oriented along the y axis. The cross-piece 262 is mounted in pivot link with the arches 261 and 263 respectively by its branches 262a and 262b.

Thus, in the Oxyz reference system, the shaft 23 is rotationally moveable around the z axis. The Cardan joint 26 enables the transmission of a torsion torque between one and the other of the shafts 23 and 28, including when they are inclined or arranged at an angle with respect to each other, and stresses along the x, y and z axes. A rotational movement of the shaft 28 around its axis will be transmitted to the shaft 23, that is to say that a torque applied to the shaft 28 will be transmitted to the shaft 23. Conversely, a rotational movement of the shaft 23 will be transmitted to the shaft 28. The three stresses transmitted along the x, y and z axes are cancelled out by the positions taken by the other links of the system, namely here the Cardan joint 27 and the pivot link 32.

Alternatively and in a non-limiting manner, the cross-piece Cardan joint 26 may be replaced by a Cardan joint of another type such as the bearing Cardan joint 27 or the ring Cardan joint 126 described hereafter or Cardan joints comprising other types of low friction pivot links such as links with metal tips on, or in, sapphires (known as 'jewel bearings').

The second Cardan joint 27 here comprises an arch 271, two pivot axes 272 and a ball bearing 273 having an internal track 273a and an external track 273b. The pivot axes 272, stick on either side in the external track of the bearing 273, connect it by pivot link to the arch 271. The pivot axes 272 are here oriented along the x axis in the position illustrated in FIG. 1a.

The internal track 273a of the ball bearing 273 delimits a receiving orifice 274 dimensioned to receive the end of a test piece 15 that it is wished to test the bending properties. The arch 261 is for example fixed to the shaft 23 or manufactured from one piece with the shaft 23. The arch 263 of the Cardan joint 26 and the arch 271 of the Cardan joint 27 are for example fixed to the arm 28 that connects them or instead manufactured one, the other or both, from one piece with the arm 28.

In the Oxyz reference system, the external track 273b is rotationally moveable around an axis merged with the x axis in the position illustrated in FIG. 1a. The interior track 273a offers an additional rotational degree of freedom along its own longitudinal axis, here transversal to the x axis. When a test piece 15 is housed in the reception orifice 274, the Cardan joint 27 enables the transformation of the torque into torsion to which the shaft 28 is subjected by traction on the actuating wire 25, into a bending moment on the test piece 15 through the intermediary of two support points, such as the points 274a and 274b described hereafter, the shaft 28 and the test piece 15 being inclined or arranged at an angle with respect to each other. A rotational movement of the shaft 28 around the axis of the test piece 15, and a torque applied to the shaft 28 around this axis, will be transmitted to the test piece 15. Conversely, a rotational movement of the test piece 15 will be transmitted to the shaft 28.

To test the bending properties of the test piece 15, said test piece 15 is placed in the attachment points formed by the orifice 32 and by the orifice 274, here by insertion of its ends in the attachment points (see FIG. 1b).

At rest, since the test piece 15 can turn in the bearing 31 with respect to the stand 30, shearing stresses along the $z_0$ axis potentially transmitted by the arm 28 result in a rotation of the bending plane of the test piece. This rotation of the bending plane of the test piece takes place until the position of the system and of the test piece 15 enables this shearing stress along $z_0$ to be cancelled out. When the test piece is rectilinear, the shearing stresses are assumed to be zero during the mounting of the test piece 15 thanks to the fine adjustment of the position of the stand 30 and to the functional clearances between the test piece 15 and the bearings 31 and 273. The initial radius of curvature of the test piece 15 therein is without importance as will be explained later with reference to plot 301.

A tension, for example vertical, is applied on the actuating wire 25. The rotational movement of the wheel 24 induced by the translational movement of the actuating wire 25 is transmitted via the Cardan joints 26 and 27 to the test piece 15. The test piece 15 then moves until it comes into contact at four points with the device 10: on the one hand the points 274a and 274b situated respectively on a first annular edge 273a1 and on a second annular edge 273a2 of the track 273a, diagonally opposed on either side of the orifice 273; on the other hand the points 32a and 32b situated respectively on a first annular edge 31a1 and on a second annular edge 31a2 of the internal track 31a of the bearing 31, diagonally opposite on either side of the orifice 32 (see points 32a, 32b, 274a, 274b in FIG. 1b). These contact points undergo and transmit stresses to the test piece resulting in "four-point" bending.

Parasitic shearing or torsion stresses on the test piece are made negligible by the different organs of the test device 10. Parasitic shearing stresses must be understood as inducing different moments from the pure bending moment, for example torsion or shear stress moments.

Figure 5A:
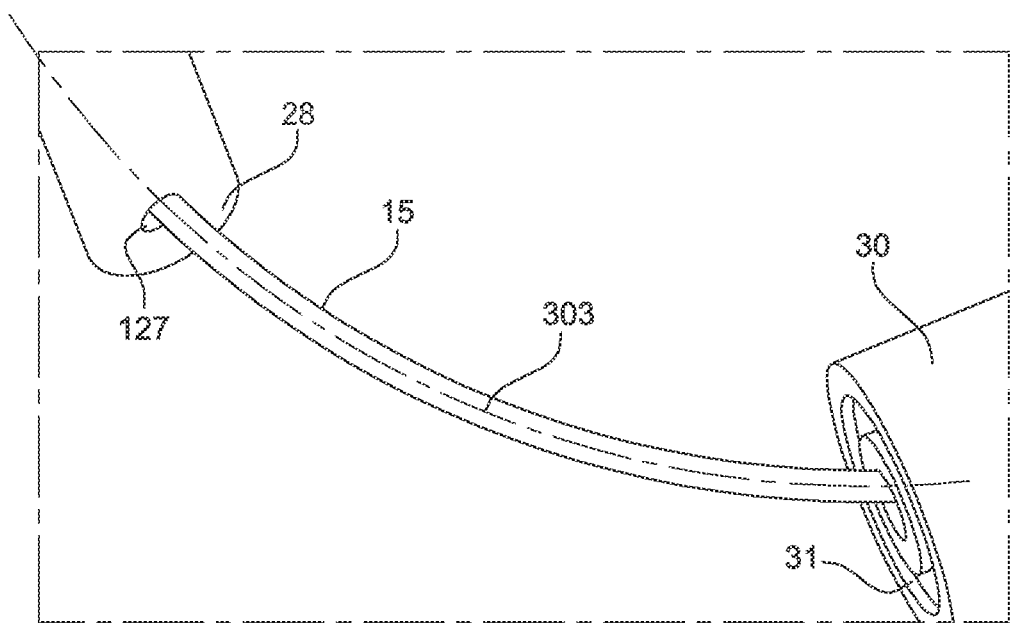
FIGS. 5a and 5b are photographs of test pieces deformed in bending in the device of FIGS. 2a to 2c.
Figure 5B:
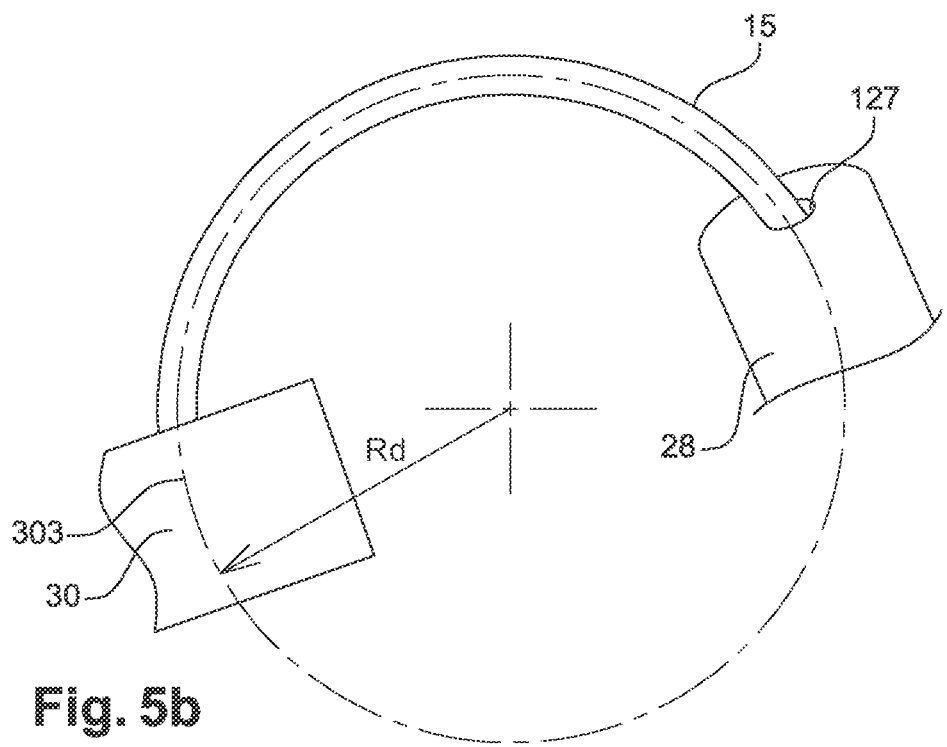

In the device 10, the parasitic stresses appearing in the test piece 15 during a bending test result from the rotating of the bearing 31, of the Cardan joint 27—of which the bearing 273- and the Cardan joint 26 (FIG. 1b). In other words, the Cardan joints 26 and 27 make it possible to make negligible in the test piece 15 both parasitic shear stresses transversally to the arm 28, that is to say along the $x_0$ and $z_0$ axes transversal to the arm 28, as illustrated in FIG. 1a, and torsion moments. The bearings 273 and 31 make it possible to minimise and to make negligible in the test piece 15 stresses along the longitudinal $z_0$ axis of the arm 28 and parasitic torsion moments. For reasons of legibility, only the wheel 24, the wire 25, the Cardan joint 27 and the support 30 are illustrated in front view in FIG. 1b. Thanks to the degrees of freedom enabled by the Cardan joints 26 and 27 and the bearing 31, the test piece 15 is subjected to a bending moment referred to as pure. The bending moment is constant at all points of the test piece. The test piece 15, in the case of a homogeneous material, is thus deformed along a perfect arc of circle between the attachment points formed by the bearings 273 and 31 (see median lines 303 of the test pieces 15 represented in FIGS. 5a and 5b with reference to the variant 11 detailed below).

This bending moment applied to the test piece 15 is then known by measuring the tension stress of the actuating wire 25, for example using a measuring cell that the traction machine comprises. An alternative solution for knowing the bending moment is to use directly an apparatus for measuring the torsion deformation of the arm 28.

In practice, low negligible friction appears in the Cardan joints 26 and 27. A considerable length L between the Cardan joints 26 and 27, here between the branch of the cross-piece 262 and the axis 272 on which the arm 28 is mounted, makes it possible to minimise further the impact of friction in the Cardan joints 26 and 27 on the measurements.

Figure 8:
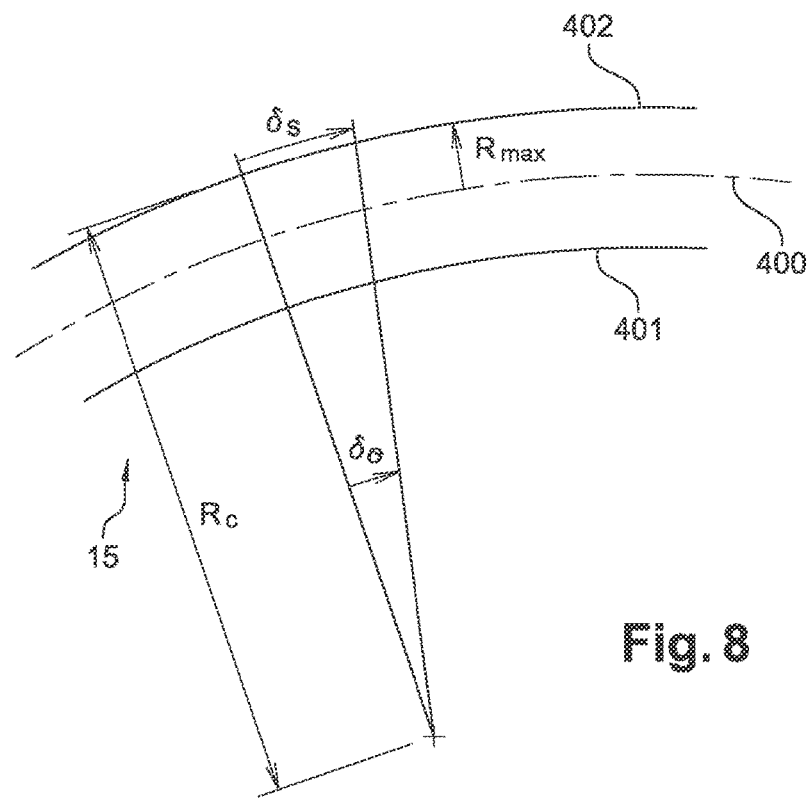
FIG. 8 is a schematic and enlarged representation of the local deformation on a test piece deformed in pure bending.

The maximum deformation $\varepsilon_{max}$ at the surface of the test piece meets the following equation: $\varepsilon_{max} = R_{max}*(\partial\theta/\partial s) = R_{max}*[(1/R_c)-(1/R_0)]$, in which the deformation $\varepsilon_{max}$ may for example be expressed in percentage, and $R_{max}$ is the radius of the test piece, $\partial\theta/\partial s$ or $(1/R_c)-(1/R_0)$ are the variation in radius of curvature between the non-deformed state and the deformed state, $\partial\theta$ is the local variation in angle between two sections of the test piece spaced apart by a distance $\theta s$, Rc is the radius of curvature attained during maximum deformation, $R_0$ is the initial radius of curvature (see FIG. 8 in which 400 is the median line on a test piece 15 in the bending plane, 401 is the interior line, deformed in compression, and 402 is the exterior line, deformed in traction).

In the present application, the term 'high deformations' corresponds to an $\varepsilon_{max}$ value greater than several %, for example 5%, or even 10% for a radius of test piece $R_{max}$ of 0.25 mm.

Figure 2A:
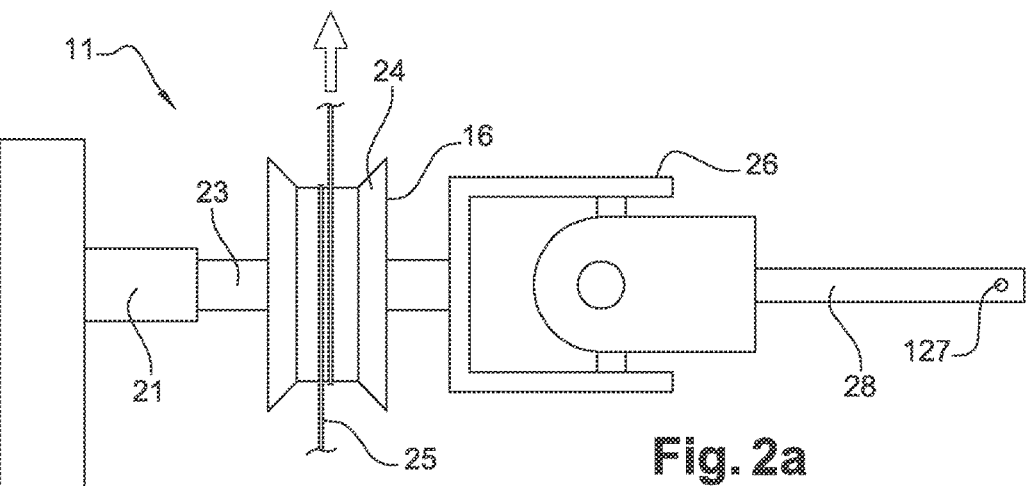

A variant 11 of the device 10 is illustrated in FIG. 2a. The elements 20 to 26 are generally the same as in the device illustrated in FIG. 1a. The Cardan joint 27 is here replaced by a simple drilling 127 made in the arm 28. The drilling 127 then forms an orifice for receiving a test piece or attachment point. The drilling 127 must be chosen of diameter greater than the diameter of the test piece 15. The functional clearances thus present between the test piece 15 and the internal surface of the drilling 127 offer the same degrees of freedom as the bearing 273 and the Cardan joint 27. Friction transversal to the test piece 15 is slightly greater but nevertheless still negligible in the measurement of the bending moment to which the test piece 15 is subjected and still makes it possible to speak of a pure bending moment.

Figure 2B:
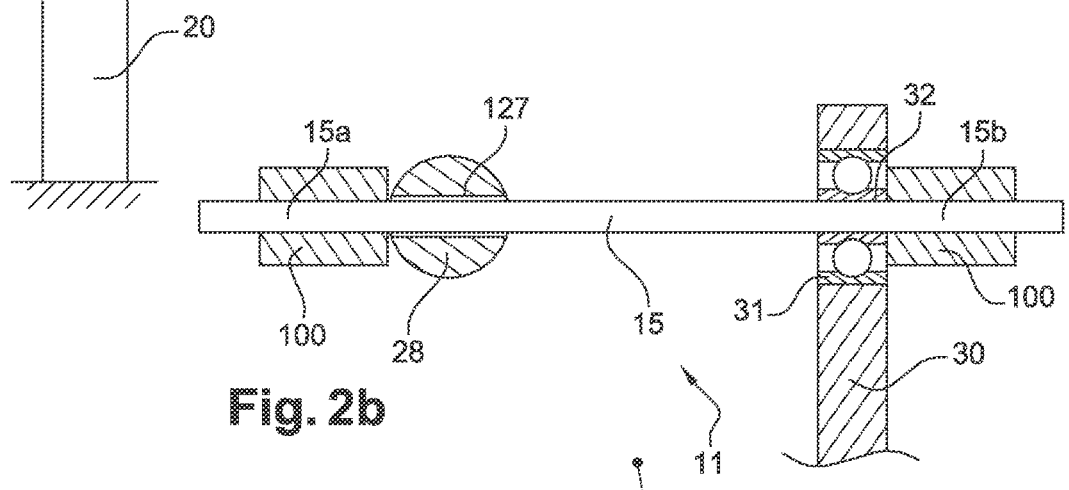
FIG. 2b is a partial front view of the device of FIG. 2a showing a test piece at rest, here rectilinear, housed in the device.
Figure 2C:
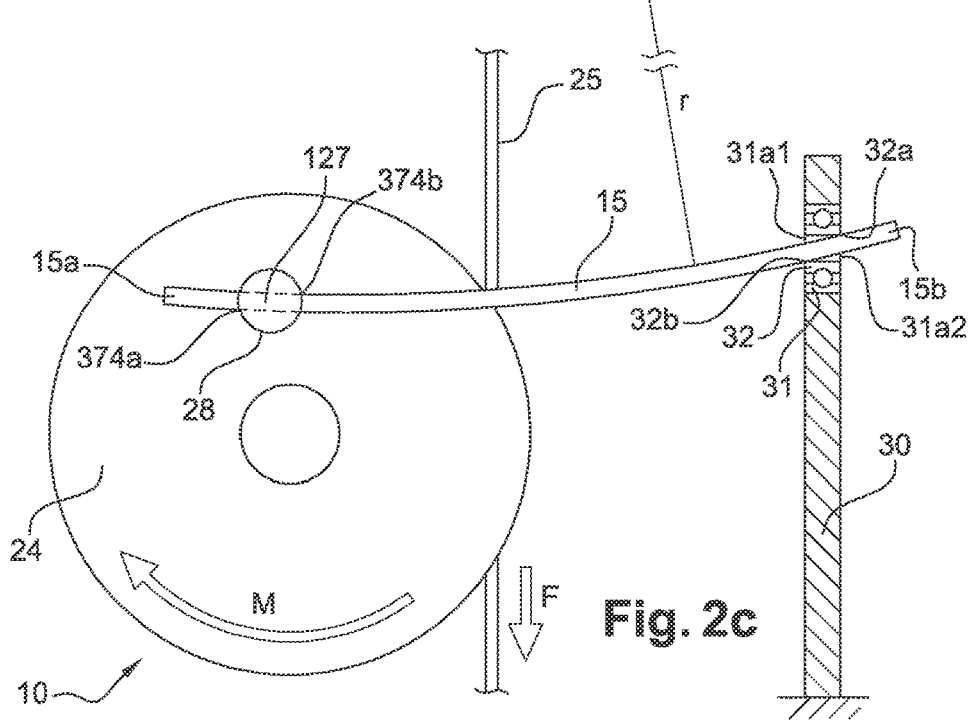
FIG. 2c is a front view of the device of FIG. 2a showing a test piece in bending.

As in the device 10, when the test piece 15 is loaded in bending in the device 11, it is in contact at four points with the device 11: the points 374a and 374b on the edges of the drilling 127 and the points 32a and 32b on the bearing 31 (see FIG. 2c).

The central section of the test piece 15, that is to say comprised between the points 374b and 32b facing each other between the arm 28 and the support 30, is subjected to a homogeneous moment. This is proved experimentally, for example by means of images, such as those reproduced schematically in FIGS. 5a and 5b. Digital processing of such images makes it possible in fact to demonstrate the circular geometry attained during bending on a test piece 15. Such a geometry is proof both of pure bending deformation and homogeneity of the material. In the particular example of FIG. 5b, the radius of curvature Rd attained is equal to 4.3 mm. An even smaller radius of curvature may be attained, the lower limit being reached when the arm 28 is in contact with the support 30.

In the sections comprised between the points 32a and 32b on the one hand and 374a and 374b on the other hand, the bending moment varies theoretically in a linear manner. The bending moment is thus not homogeneous therein. The deformation of the test piece 15 between the points 374a and 374b (respectively 32a and 32b) results in a contact at different angle between the test piece 15 and the contact surface at each of the points 374a and 374b. This difference in angle may thus induce stresses along the axis of the test piece between the points 374a and 374b.

Advantageously, rings 100 may thus be provided, tightened onto the ends of the test piece 15, against the arm 28 and the stand 30, outside of the zone comprised between the arm 28 and the stand 30 (FIG. 2b). The rings 100 have the role of preventing longitudinal sliding of the test piece 15 by adding a longitudinal force against the circumference of the drilling 127 making it possible to balance the normal stresses in 374a and 374b (respectively 32a and 32b) respectively. The rings 100 thus make it possible to conserve a constant length of test piece 15 between the bearings 21 and 31 during the bending test.

Another variant 12 of the device 10 is illustrated in FIGS. 3a and 3b. Elements similar to the embodiments described previously bear the same references in the figures and are not described again.

In this variant 12, the pulley system 116, the Cardan joint 126 and the structures 123 and 128 are substituted by the system 16, the Cardan joint 26, the shaft 23 and the arm 28 of the device 10.

The structure 123 comprises a shaft 1231 and a sleeve 1232. The shaft 1231 is fixed onto the stand 20. The sleeve 1232 is mounted in pivot link on the shaft 1231, through the intermediary of a bearing, for example a ball bearing, not represented.

The pulley system 116 comprises a wheel 124. Two openings 1241 traverse the wheel 124 longitudinally, between its two lateral faces.

The wheel 124 is fixed onto the sleeve 1232.

The structure 128 comprises an arm 1280, two branches 1281, a balancing mass 1282, here in the form of two balance weights. The arm 1280 is connected at one end to the Cardan joint 27.

At the end of the arm 1280 opposite to the joint 27, the two branches 1281 extend in a fork shape, symmetrically, that is to say in mirror image, with respect to the plane yz. Each branch 1281 here has from the arm 1280 a skewed portion, a portion parallel to the arm 1280 and finally another skewed portion, here in a non-limiting manner parallel to the first skewed portion. Each branch 1281 traverses a respective opening 1241 of the wheel 124. Thanks to the Cardan joint 126 described hereafter, the branches 1281 are rotationally moveable around two axes transversal to the longitudinal axis of the sleeve 1232, and transversal to each other.

Each branch 1281 here bears a balance weight 1282 at its distal end, opposite to the arm 1280. The balance weights 1282 counterbalance the weight of the arm 1280 so that in the absence of the test piece 15, the arm 1280 is either at equilibrium, or substantially horizontal. In other words, the balance weights 1282 make it possible to make negligible the influence of the own weight of the arm 1280 and the Cardan joint 27.

The balancing masses 1282 may be replaced by other balancing masses such as an annular element connecting the branches 1281.

Figure 6:
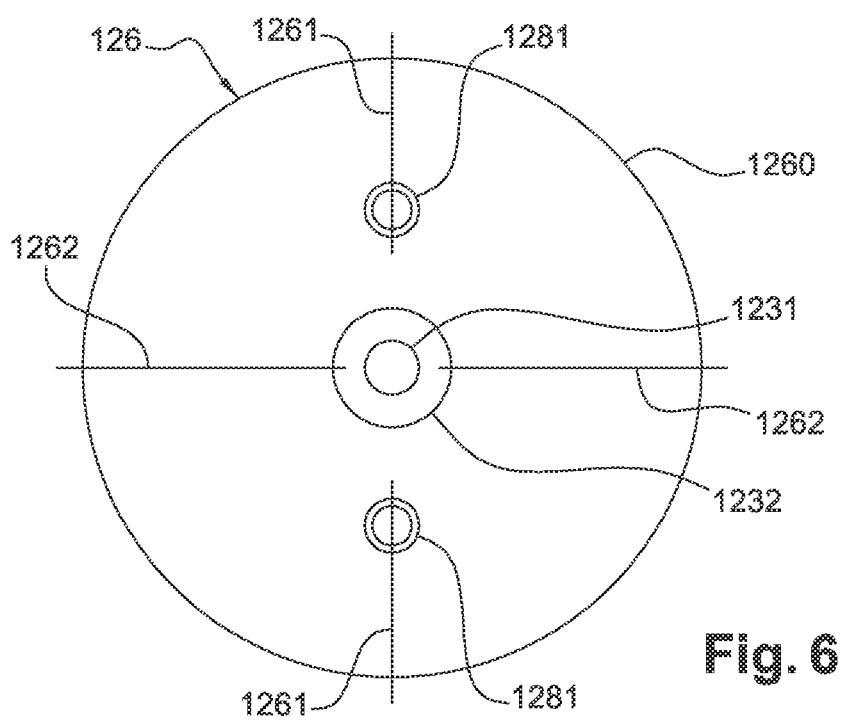
FIG. 6 is a diagram of a Cardan joint implemented in the variant of the device illustrated in FIGS. 3a and 3b.

The Cardan joint 126 here comprises a ring 1260, two pivot axes 1261 and two pivot axes 1262 (see FIG. 6). The pivot axes 1261 and 1262 have for example but in a non-limiting manner a needle shape. The axes 1262 connect by pivot link the ring 1260 to the sleeve 1232. The axes 1261 connect by pivot link the ring 1260 to each of the branches 1281 on the side of the pulley 16 opposite to the Cardan joint 27. This advantageously makes it possible to increase the length L between the Cardan joints 126 and 27, that is to say here between the axes 1261 and the axis 272, while conserving a size of the device 12 similar to that of the device 10. The dimensions of the figures are not limiting. It is possible for example to choose an arm 28 or 1280 of greater length.

Figure 7:
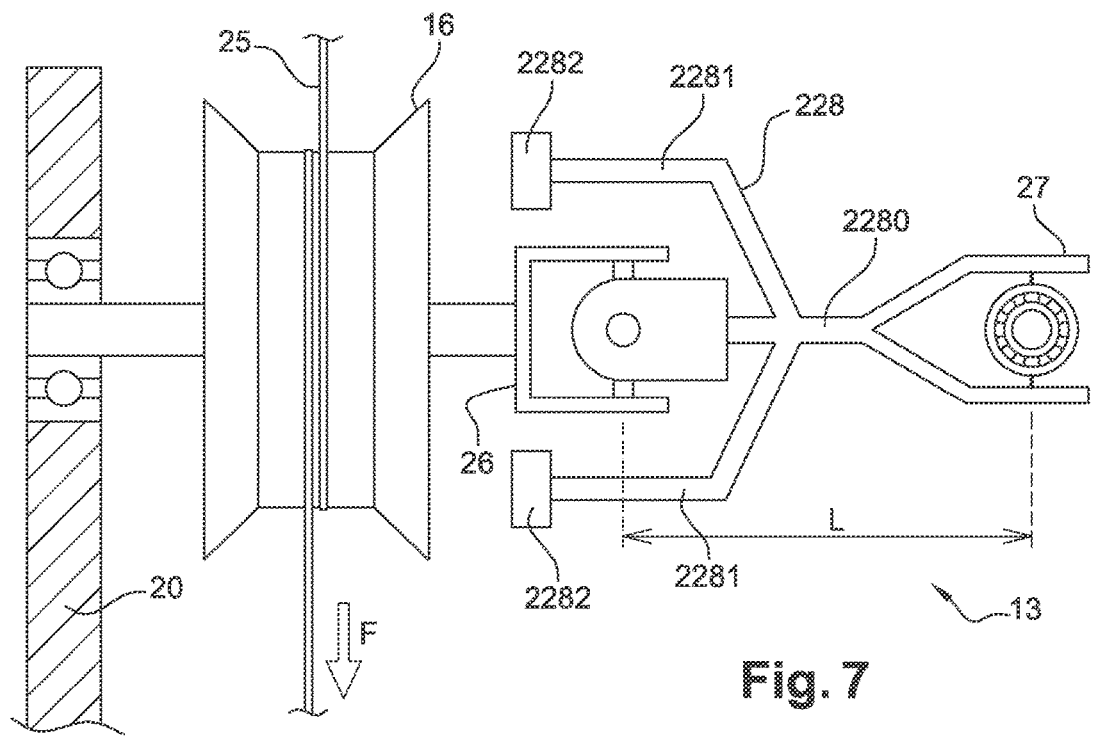

Another variant 13 of the device 10 is illustrated in FIG. 7.

In this variant, the stand 20, the pulley 16, the Cardan joints 26 and 27 are the same as described previously.

The device 13 comprises a structure 228 similar to the structure 128 described above. The structure 228 comprises an arm 2280 that links the Cardan joints 26 and 27, two branches 2281 which extend in a fork shape on either side of the arm 2280, a balancing mass 2282, here in the form of two balance weights borne respectively by each branch 2281 at its distal end, opposite to the arm 2280. The branches 2281 do not here traverse the wheel of the pulley 16. The balance weights 2282 have the same role of balancing the arm 2280 with respect to the Cardan joint 26 as the balance weights 1282 with respect to the Cardan joint 126.

Other embodiments are also possible, for example by combining in a same bending test device the Cardan joint 126 and the simple drilling 127.

In all the embodiments described, rings 100 may be implemented with the same advantages as described previously.

Figure 4:
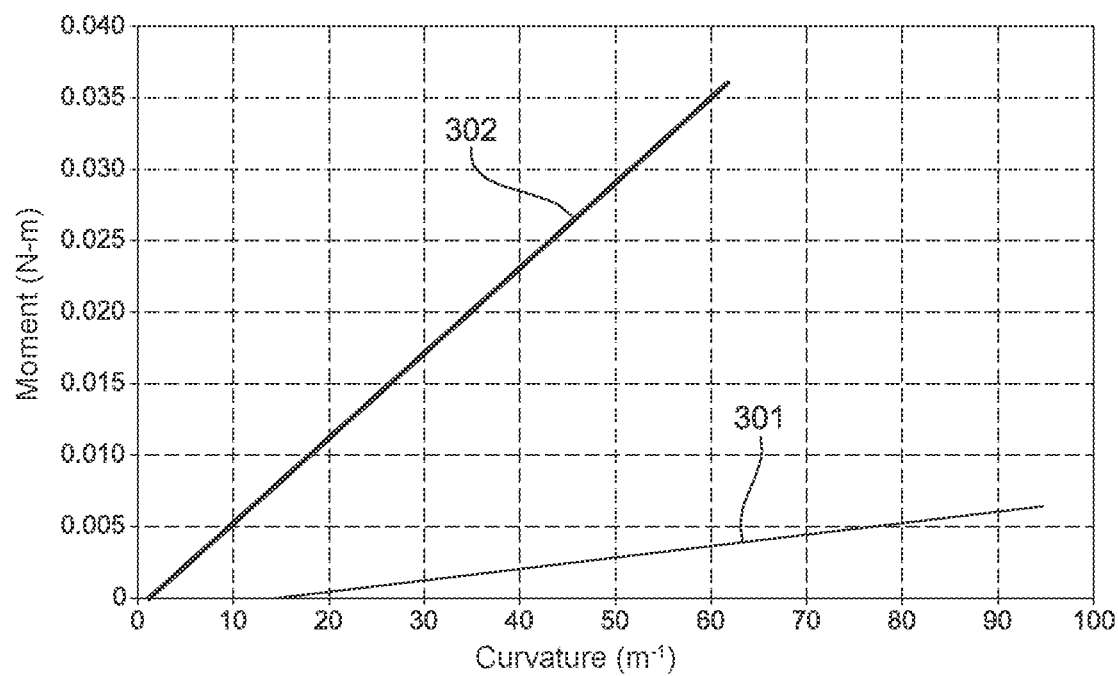
FIG. 4 is a plotting of measurements taken during a bending test for two steel wires of different diameter.

The above devices have been tested and validated experimentally. Two plots 301 and 302 illustrated in FIG. 4 have been obtained during a bending test in the elastic domain (thus linear) of two test pieces, here steel wires. The first plot 301 has been obtained by testing a slender steel wire of 0.3 mm diameter, a second plot 302 has been obtained by testing a slender steel wire of 0.5 mm diameter.

The curvature, or more precisely the variation in curvature compared to the original curvature, is read on the x axis, whereas the corresponding bending moment is read on the y axis.

The different points of these plots 301 and 302 have been obtained on the one hand by measuring the bending moment applied to the wire concerned as explained above, and on the other hand by measuring the radius of curvature in photographs or images taken at corresponding instants.

It may be seen that the plot 301 is shifted with respect to the origin of the graph and has as starting point a curvature of around 15 $m^{-1}$. In fact, the sample is stored in reel form and has a non-zero initial radius of curvature. In practice, said initial radius of curvature only has the impact of shifting the curve. The plot 301 could be easily corrected by deducing, from all the values read (1/Rc), the value 1/Ro, where Ro is the initial radius of curvature of the test piece 15. The test piece 15, when it initially comprises a non-zero curvature, once mounted in the system, will naturally tend to find a position making it possible to minimise both its elastic potential energy and the elastic potential energy of the whole system thanks to the degrees of freedom that offer for example the bearings 273 and 31. The test piece 15 will then deform from this position of lowest elastic potential energy.

To obtain the plot 301, the test device 10 has been used up to a curvature of the order of 95 $m^{-1}$, i.e. a radius of curvature of $1/95$ m, that is to say around 1.05 cm.

Experimental tests have validated the use of the device 10 up to a radius of curvature of 7 mm for other materials having better bending properties than steel.

Depending on the shape and the dimension of the elements of the devices 10, 11, 12 or variants thereof, even smaller radiuses of curvature may be obtained up to the point that the means for holding the two ends of the test piece 15, such as the bearing 273, the shaft 28 provided with the drilling 127 or the bearing 31, touch each other.

What is claimed is:

1. A device for performing a mechanical four-point bending test on a test piece, said device comprising:
    a) a bearing for holding a first end of the test piece and means for holding a second end of the test piece;
    b) traction means and converting means for converting a translational movement of said traction means into a rotational movement; and
    c) a first Cardan joint for converting said rotational movement into bending deformation of the test piece, the first Cardan joint being connected to the bearing.

2. The device according to claim 1, further comprising a second Cardan joint for converting said rotational movement into bending deformation of the test piece.

3. The device according to claim 2, the second Cardan joint comprising the bearing.

4. The device according to claim 1, the converting means for converting the translational movement of said traction means into the rotational movement comprising a wheel, the first Cardan joint connecting the wheel and the bearing.

5. The device according to claim 1, the first Cardan joint being connected to a structure that traverses the converting means for converting the translational movement of said traction means into the rotational movement.

6. The device according to claim 5, the structure comprising two branches arranged in a fork shape, the converting means for converting the translational movement of said traction means into the rotational movement comprising a wheel, the wheel being provided with two through openings, each branch traversing respectively one of the two openings.

7. The device according to claim 5, the structure further comprising balancing means.

8. The device according to claim 7, the balancing means comprising at least one balancing mass.

9. The device according to claim 1, further comprising means for measuring stress exerted on the traction means.

10. A mechanical bending test system, comprising a traction machine and a mechanical bending test device according to claim 1, the traction machine comprising a traction mechanism connected to the traction means of the test device, the mechanism being configured to apply a traction force on these traction means.

11. A method for performing a mechanical bending test on a test piece using a mechanical bending test device according to claim 1, comprising the steps of:
    placing the first end of the test piece in the bearing and placing the second end of the test piece in the means for holding the second end of the test piece;

applying a tension on the traction means; and determining the bending moment by means for measuring stress exerted on the traction means.

12. The method according to claim 11, further comprising the steps of:

tightening a first ring onto the first end of the test piece, against the bearing; and tightening a second ring onto the second end of the test piece, against the means for holding the second end of the test piece the first and second rings being tightened onto the respective ends of the test piece outside of a zone comprised between the bearing and the means for holding the second end of the test piece.

13. The method according to claim 11, in which the test piece is slender.

14. The method according to claim 11, in which the test piece attains a surface deformation of at least 3%.

15. The method according to claim 11, in which the test piece attains a surface deformation of at least 5%.

16. A device for performing a mechanical four-point bending test on a test piece, said device comprising:

a) a shaft with a hole formed therein, the hole configured to receive and hold a first end of the test piece;

b) means for holding a second end of the test piece;

c) traction means and converting means for converting a translational movement of said traction means into a rotational movement; and d) a first Cardan joint for converting said rotational movement into bending deformation of the test piece, the first Cardan joint being connected to the shaft.

17. The device according to claim 16, the converting means for converting the translational movement of said traction means into the rotational movement comprising a wheel, the first Cardan joint connecting the wheel and the shaft.

18. The device according to claim 16, the first Cardan joint being connected to a structure that traverses the converting means for converting the translational movement of said traction means into the rotational movement.

19. The device according to claim 18, the structure further comprising balancing means.

20. The device according to claim 16, further comprising means for measuring stress exerted on the traction means.

* * * * *